United States Patent [19]
Flockerzi

[11] Patent Number: 6,143,759
[45] Date of Patent: Nov. 7, 2000

[54] TETRAZOLES

[75] Inventor: Dieter Flockerzi, Allensbach, Germany

[73] Assignee: BYK Gulden Lomberg Chemische Fabrik GmbH, Constance, Germany

[21] Appl. No.: 09/367,852

[22] PCT Filed: Mar. 3, 1998

[86] PCT No.: PCT/EP98/01168
 § 371 Date: Aug. 30, 1999
 § 102(e) Date: Aug. 30, 1999

[87] PCT Pub. No.: WO98/40382
 PCT Pub. Date: Sep. 17, 1998

[30] Foreign Application Priority Data

Mar. 7, 1997 [DE] Germany ............................. 197 09 293
 Mar. 8, 1997 [AT] Austria .................................. 97103924

[51] Int. Cl.[7] ....................... A61K 31/4375; A61P 11/00; C07D 471/04
[52] U.S. Cl. .............................................. 514/292; 546/81
[58] Field of Search ................................ 546/81; 514/292

[56] References Cited

U.S. PATENT DOCUMENTS 3,899,494 8/1975 Ott et al. .............................. 260/287 R
5,346,904 9/1994 Flockerzi et al. ........................ 514/292

*Primary Examiner*—Evelyn Mei Huang
*Attorney, Agent, or Firm*—Jacobson, Price, Holman & Stern, PLLC

[57] ABSTRACT

Compounds of formula (I) in which $R^4$ is a phenyl radical substituted by $R^5$, where $R^5$ is a tetrazole-5-yl-radical optionally substituted by a radical $R^6$, are novel efficacious PDE3/4 inhibitiors.

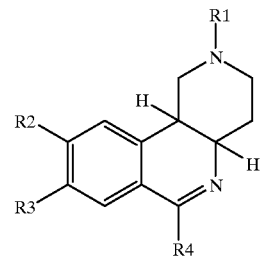

(I)

12 Claims, No Drawings

TETRAZOLES

This application is the national phase of PCT/EP98/01168, filed Mar. 3, 1998.

FIELD OF APPLICATION OF THE INVENTION

The invention relates to novel 6-[(tetrazol-5-yl)phenyl] benzonaphthyridines, which are used in the pharmaceutical industry for the production of medicaments.

KNOWN TECHNICAL BACKGROUND

DE-A 21 23 328 and U.S. Pat. No. 3,899,494 describe substituted benzonaphthyridines which are distinguished by marked inhibition of blood platelet aggregation. EP 247 971 and WO91/17991 disclose 6-phenylbenzonaphthyridines for the treatment of inflammatory airway disorders.

DESCRIPTION OF THE INVENTION

It has now been found that the following compounds of the formula I described in greater detail below, which differ from the compounds of EP 247 971 and WO91/17991, in particular, by the substitution on the 6-phenyl ring, have surprising and particularly advantageous properties.

The invention thus relates to compounds of the formula I (I)

in which

R1 is 1–4C-alkyl,

R2 is hydroxyl, 1–4C-alkoxy, 3–7C-cycloalkoxy, 3–7C-cycloalkylmethoxy, or 1–4C-alkoxy which is completely or predominantly substituted by fluorine, R3 is hydroxyl, 1–4C-alkoxy, 3–7C-cycloalkoxy, 3–7C-cycloalkylmethoxy, or 1–4C-alkoxy which is completely or predominantly substituted by fluorine, or in which R2 and R3 together are a 1–2C-alkylenedioxy group, R4 is a phenyl radical substituted by R5, where R5 is a tetrazol-5-yl radical substituted by a radical R6, where R6 is hydrogen, 1–10C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, and the salts of these compounds.

One embodiment of the invention are compounds of the formula I, in which

R1 is 1–4C-alkyl,

R2 is hydroxyl, 1–4C-alkoxy, 3–7C-cycloalkoxy, 3–7C-cycloalkylmethoxy, or 1–4C-alkoxy which is completely or predominantly substituted by fluorine, R3 is hydroxyl, 1–4C-alkoxy, 3–7C-cycloalkoxy, 3–7C-cycloalkylmethoxy, or 1–4C-alkoxy which is completely or predominantly substituted by fluorine, or in which R2 and R3 together are a 1–2C-alkylenedioxy group, R4 is a phenyl radical substituted by R5, where R5 is a tetrazol-5-yl radical substituted by a radical R6, where R6 is hydrogen, 1–7C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, and the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which in addition to the oxygen atom contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Examples of 1–4C-alkoxy which is completely or predominantly substituted by fluorine are the 2,2,3,3,3-pentafluoropropoxy, the perfluoroethoxy and the 1,2,2-trifluoroethoxy radicals, in particular the 1,1,2,2-tetrafluoroethoxy, the trifluoromethoxy, the 2,2,2-trifluoroethoxy and, preferably, the difluoromethoxy radicals.

1–2C-Alkylenedioxy represents, for example, the methylenedioxy radical (—O—$CH_2$—O—) and the ethylenedioxy radical (—O—$CH_2$—$CH_2$—O—).

1–10C-Alkyl represents straight-chain or branched alkyl radicals having 1 to 10 carbon atoms. Examples which may be mentioned are the decyl, nonyl, octyl, heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-Cycloalkyl represents the cyclopropyl, cyclobutyl, cyclopentyl, cyclohexyl and cycloheptyl radicals. The 5–7C-cycloalkyl radicals cyclopentyl, cyclohexyl and cycloheptyl may be preferably mentioned.

3–7C-Cycloalkylmethyl represents a methyl radical which is substituted by one of the abovementioned 3–7C-cycloalkyl radicals. Examples which may be mentioned are the cyclopentylmethyl and the cyclohexylmethyl radicals.

Ar-1–4C-alkyl represents one of the abovementioned 1–4C-alkyl radicals which is substituted by one of the aryl radicals defined above. Examples which may be mentioned are the p-methoxybenzyl, the phenethyl and the benzyl radicals.

Suitable salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand—for example in the case of a 1H- or 2H-tetrazol-5-yl substitution—salts with bases are also suitable. Examples of salts with bases which may be mentioned are alkali metal (lithium, sodium, potassium) or calcium, aluminium, magnesium, titanium, ammonium, meglumine or guanidinium salts, where here too the bases are employed in salt preparation in an equimolar quantitative ratio or one differing therefrom.

Pharmacologically intolerable salts, which are obtained initially as process products, for example in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those in which

R1 is 1–2C-alkyl,

R2 is 1–4C-alkoxy, 3–7C-cycloalkoxy, 3–7C-cycloalkylmethoxy, or 1–4C-alkoxy which is completely or predominantly substituted by fluorine, R3 is 1–4C-alkoxy, 3–7C-cycloalkoxy, 3–7C-cycloalkylmethoxy, or 1–4C-alkoxy which is completely or predominantly substituted by fluorine, or in which R2 and R3 together are a 1–2C-alkylenedioxy group, R4 is a phenyl radical substituted by R5, where R5 is a tetrazol-5-yl radical substituted by a radical R6, where R6 is hydrogen, 1–7C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, and the salts of these compounds.

Compounds of the formula I to be particularly emphasized are those in which

R1 is methyl,

R2 is 1–4C-alkoxy, 3–7C-cycloalkoxy, 3–7C-cycloalkylmethoxy, or 1–2C-alkoxy which is completely or predominantly substituted by fluorine, R3 is 1–4C-alkoxy, 3–7C-cycloalkoxy, 3–7C-cycloalkylmethoxy, or 1–2C-alkoxy which is completely or predominantly substituted by fluorine, R4 is a phenyl radical substituted by R5, where R5 is a tetrazol-5-yl radical substituted by a radical R6, where R6 is hydrogen, 1–7C-alkyl, 5–7C-cycloalkyl, 3–7C-cycloalkylmethyl or Ar-1–2C-alkyl, where Ar is a phenyl radical which is unsubstituted or substituted by R7, and R7 is 1–2C-alkyl or 1–2C-alkoxy, and the salts of these compounds.

Preferred compounds of the formula I are those in which

R1 is methyl,

R2 is 1–4C-alkoxy,

R3 is 1–4C-alkoxy,

R4 is a phenyl radical substituted by R5, where

R5 is a tetrazol-5-yl radical substituted by a radical R6, where

R6 is hydrogen, 1–7C-alkyl, cyclohexylmethyl or 4-methoxybenzyl, and the salts of these compounds.

One embodiment of the preferred compounds of the formula I are those compounds in which R1 is methyl, R2 is methoxy or ethoxy, R3 is methoxy or ethoxy, R4 is a phenyl radical substituted by R5, where R5 is a tetrazol-5-yl radical substituted by a radical R6, where R6 is hydrogen, methyl, ethyl, cyclohexylmethyl or 4-methoxybenzyl, and the salts of these compounds.

Especially preferred compounds of the formula I are those in which

R1 is methyl,

R2 is ethoxy,

R3 is methoxy or ethoxy,

R4 is a phenyl radical substituted by R5, where

R5 is a tetrazol-5-yl radical substituted by a radical R6, where

R6 is hydrogen, methyl, ethyl, propyl, hexyl, cyclohexylmethyl or 4-methoxybenzyl, and the salts of these compounds.

The compounds of the formula I are chiral compounds having chiral centers in positions 4a and 10b

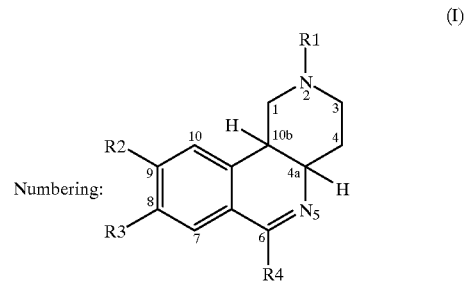

The invention therefore both comprises all conceivable pure diastereomers and pure enantiomers, and their mixtures in any mixing ratio, including the racemates. Preferred compounds of the formula I are those in which the hydrogen atoms in the positions 4a and 10b are cis to one another. The pure cis enantiomers are particularly preferred.

In this connection, particularly preferred compounds of the formula I are those which have the same absolute configuration in positions 4a and 10b as the compound (−)-cis-4-amino-3-(3,4-dimethoxyphenyl)-1-methylpiperidine dihydrochloride with the optical rotation $[\alpha]_D^{22} = -57.1°$ (c=1, methanol) which can be employed as a starting material and is described in DE 42 17 401.

The enantiomers can be separated in a known manner (for example by preparation and separation of corresponding diastereoisomeric compounds) or can be prepared by stereoselective synthesis methods. Such separation processes and synthesis methods are described, for example, in EP 247 971 and in DE 42 17 401.

The tetrazol-5-yl radical R5 of the compounds of the formula I can be bonded to the phenyl radical R4 either in the ortho-, meta- or para-position relative to the benzonaphthyridine ring.

Preferred compounds of the formula I are those in which the tetrazol-5-yl radical R5 is bonded to the phenyl radical R4 in the meta- or para-position relative to the benzonaphthyridine ring. Particularly preferred compounds of the formula I in this connection are those in which the tetrazol-5-yl radical R5 is bonded in the para-position.

Compounds of the formula I in which R1, R2, R3, R4 and R5 have the meanings indicated above and R6 is hydrogen occur in two tautomeric forms which are in equilibrium with one another (1H and 2H form of the tetrazol-5-yl radical). The invention therefore comprises both tautomeric forms in any mixing ratio.

By bonding of the substituents R6 (R6≠H) to the tetrazol-5-yl group, the conversion of the two tautomeric forms into one another is blocked. The invention therefore also relates to the 1H- and 2H-tetrazol-5-yl compounds of the formula I substituted by a radical R6 (R6≠H), both in pure form and in any mixing ratio. However, the compounds of the formula I are preferred in which the tetrazol-5-yl radical is substituted in the 2-position by one of the radicals R6 (R6≠H).

The invention further relates to a process for the preparation of the compounds of the formula I, in which R1, R2, R3 and R4 have the meanings indicated above, and their salts.

The process is characterized a) in that for the preparation of compounds of the formula I, in which R1, R2 and R3 have the meanings indicated above, R4 is a phenyl radical substituted by a tetrazol-5-yl radical R5, which itself is substituted by R6=hydrogen, the corresponding compounds of the formula I, in which R1, R2 and R3 have the meanings indicated above and R4 is a phenyl radical substituted by a cyano group, are reacted with an alkali metal azide and a halogen salt of ammonia, or b) in that for the preparation of compounds of the formula I, in which R1, R2 and R3 have the meanings indicated above, R4 is a phenyl radical substituted by a tetrazol-5-yl radical R5, which itself is substituted by R6≠hydrogen, the corresponding compounds of the formula II

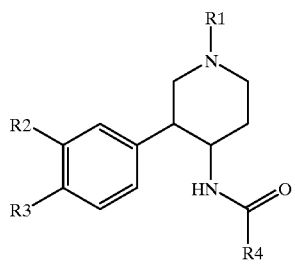

(II)

are subjected to a cyclocondensation, and in that, if desired, compounds of the formula I obtained according to a) or b) are then converted into their salts, or in that, if desired, salts of the compounds of the formula I obtained according to a) or b) are then converted into the free compounds.

If desired, compounds of the formula I obtained can be converted by derivatization into further compounds of the formula I. For example, compounds of the formula I, in which R4 is a phenyl radical substituted by R5 and R6 is an unsubstituted H- or 2H-tetrazol-5-yl radical, can be converted by alkylation reactions into the corresponding substituted tetrazole compounds of the formula I, where the hydrogen of the tetrazole ring is replaced by the radicals mentioned for R6—excluding hydrogen. The reactions are expediently carried out analogously to the methods known to the person skilled in the art, e.g. by reaction of the 1H- or 2H-tetrazole compounds of the formula I with compounds of the formula R6-X in the presence of a base, where R6 has the abovementioned meanings—excluding hydrogen—and X is a suitable leaving group such as, for example, a chlorine, bromine or iodine atom or an alkylsulfate radical. The 1- and 2-substituted tetrazole regioisomer mixtures usually formed in the alkylation are separated on suitable support materials by methods known to the person skilled in the art, such as crystallization or chromatography. An analogous alkylation of tetrazoles and separation of the regioisomers is described, for example, in J. Med. Chem. 1996, 39, 2354.

The cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling temperature of the solvent or condensing agent used.

Compounds of the formula II in which R1, R2, R3 and R4 have the meanings indicated above are accessible from the corresponding compounds of the formula III.

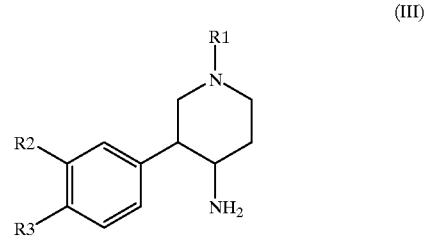

(III)

in which R1, R2 and R3 have the meanings indicated above, by reaction with compounds of the formula R4—CO—Y in which R4 has the meaning indicated above and Y is a suitable leaving group, preferably a chlorine atom. For example, the benzoylation as described in the following examples is carried out by the Einhorn process, the Schotten-Baumann variant or as described in J. Chem. Soc. (C), 1971, 1805–1808.

Compounds of the formula R4—CO—Y are either known or can be prepared from the corresponding carboxylic acids R4—COOH, in which R4 has the meaning indicated above, by reaction in a manner familiar to the person skilled in the art.

The compounds R4—COOH, in which R4 has the meaning indicated above, are either known or can be obtained from alkyl 2-, 3- or 4-cyanobenzoates in a manner known to the person skilled in the art, e.g. by reaction with alkali metal azides and halogen salts of ammonia to give alkyl 2-, 3- or 4-(1H- or 2H-tetrazol-5-yl)benzoates unsubstituted in the tetrazole moiety. A reaction of this type is described, for example, in J. Med. Chem. 1993, 36, 3246. If desired, these intermediate compounds can be converted—as described above for the 1H- or 2H-tetrazole compounds of the formula I or in the abovementioned literature—by alkylation with compounds of the formula R6-X in the presence of a base into alkyl R4-carboxylates in which R4 is a phenyl radical substituted by R5, R5 is a 1H- or 2H-tetrazol-5-yl radical substituted by a radical R6 and R6 is not hydrogen, but has one of the other meanings mentioned above for R6. By means of alkaline or acidic hydrolysis conditions familiar to the person skilled in the art, the alkyl R4-carboxylates are converted into the free carboxylic acids R4—COOH.

The preparation of cis/trans racemate mixtures and of pure cis racemates of compounds of the formula III is described, for example, in U.S. Pat. No. 3,899,494, in DE-A 21 23 328 and in DE-A 16 95 782. Pure cis enantiomers of the compounds of the formula III can be obtained, for example, by the processes such as are disclosed in EP 0 247 971 and in DE 42 17 401.

The substances according to the invention are isolated and purified in a manner known per se, for example by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating using a nonsolvent for the addition salt or by evaporation of the solvent. Salts obtained can be converted by alkalization or by acidification into the free compounds, which in turn can be converted into salts. In this manner, pharmacologically intolerable salts can be converted into pharmacologically tolerable salts.

The following examples serve to illustrate the invention in greater detail without restricting it. Likewise, further compounds of the formula I, whose preparation is not described explicitly, can be prepared in an analogous manner or in a manner familiar per se to the person skilled in the art using customary process techniques.

In the examples, m.p. stands for melting point, h for hour(s), RT for room temperature, EF for empirical formula, MW for molecular weight, calc. for calculated. The compounds and their salts mentioned in the examples are a preferred subject of the invention.

EXAMPLES

Final Products 1. (−)-cis-8,9-Dimethoxy-2-methyl-6-[4-(1H- and 2H-tetrazol-5-yl)phenyl]-1,2,3,4,4a,10b-hexahydrobenzo[c][1,6]naphthyridine 6.87 g of (−)-cis-6-(p-cyanophenyl)-8,9-dimethoxy-2-methyl-1,2,3,4,4a,10b-hexahydrobenzo[c][1,6]naphthyridine (starting compound A), 1.37 g of sodium azide and 0.26 g of ammonium chloride are heated to 110° C. for 35 h in 40 ml of DMF under an atmosphere of nitrogen. After distilling off the bulk of the DMF, the residue is partitioned between saturated sodium hydrogencarbonate solution and n-butanol. The organic phase is washed with water and concentrated. The solid residue is purified by silica gel chromatography, and the main product fraction is separated and concentrated. The solid foamed residue is washed with stirring with a 1:1 mixture of diethyl ether and petroleum ether and filtered off with suction. 3.85 g of the title compound are obtained as a fine slightly yellowish powder of m.p. 215–220° C. (unsharp).

EF: $C_{22}H_{24}N_6O_2$ MW: 404.47

Optical rotation: $[\alpha]_D^{20}$=−76.9° (c=1, methanol).

2. (−)-cis-8,9-Dimethoxy-2-methyl-6-[4-(2H-2-ethyltetrazol-5-yl)phenyl]-1,2,3,4,4a,10b-hexahydrobenzo[c][1,6]naphthyridine hydrochloride 1.72 g of (−)-cis-3-(3,4-dimethoxyphenyl)-4-[4-(2H-2-ethyltetrazol-5-yl)benzamido]-1-methylpiperidine (starting compound E) are heated to boiling under reflux for 16 h in 6 ml of phosphorus oxychloride and 20 ml of acetonitrile. After distilling off the excess phosphorus oxychloride, the residue is partitioned between dichloromethane and saturated sodium hydrogencarbonate solution. The organic phase is washed with water, dried over sodium sulfate and concentrated. The solid residue is purified by silica gel chromatography, and the main product fraction is separated and concentrated. The solid residue is dissolved in a little methanol, and the solution is treated with one equivalent of aqueous HCl and concentrated. The solid residue is recrystallized in methanol/diethyl ether.

EF: $C_{24}H_{28}N_6O_2 \times 1.3$ HCl$\times 1.2$ $H_2O$, MW: 501.55

Optical rotation: $[\alpha]_D^{20}$=−31.2° (c=1, methanol).

Starting from the corresponding starting compounds F to W (described below), the following title compounds are obtained analogously to Example 2:

3. (−)-cis-8,9-Diethoxy-2-methyl-6-[4-(2H-2-ethyltetrazol-5-yl)phenyl]-1,2,3,4,4a,10b-hexahydrobenzo[c][1,6]naphthyridine hydrochloride EF: $C_{26}H_{32}N_6O_2 \times$HCl$\times 0.95$ $H_2O$, MW: 514.17; m.p. 177–180° C. (unsharp)

Optical rotation:

$$[\alpha]_D^{20} = -62.1° (c = 1, \text{methanol}).$$

4. (−)-cis-8,9-Dimethoxy-2-methyl-6-[4-(2H-2-methyltetrazol-5-yl)phenyl]-1,2,3,4,4a,10b-hexahydrobenzo[c][1,6]naphthyridine EF: $C_{23}H_{26}N_6O_2$, MW: 418.50; m.p. 194° C.

Optical rotation:

$$[\alpha]_D^{20} = -121.0° (c = 1, \text{methanol}).$$

5. (−)-cis-8,9-Diethoxy-2-methyl-6-[[4-[2H-2-(4-methoxybenzyl)tetrazol-5-yl]-phenyl]]-1,2,3,4,4a,10b-hexahydrobenzo[c][1,6]naphthyridine hydrochloride EF: $C_{32}H_{36}N_6O_3 \times 1.15$ HCl$\times 0.75$ $H_2O$, MW: 608.12; m.p. 139–145° C. (unsharp)

Optical rotation:

$$[\alpha]_D^{20} = -17.4° (c = 1, \text{methanol}).$$

6. (−)-cis-8,9-Diethoxy-2-methyl-6-[4-(2H-2-methyltetrazol-5-yl)phenyl]-1,2,3,4,4a,10b-hexahydrobenzo[c][1,6]naphthyridine hydrochloride EF: $C_{25}H_{30}N_6O_3 \times 1.15$ HCl$\times H_2O$, MW: 506.50; m.p. 161–168° C. (unsharp)

Optical rotation:

$$[\alpha]_D^{20} = -34.7° (c = 1, \text{methanol}).$$

7. (−)-cis-8,9-Dimethoxy-2-methyl-6-[[4-[2H-2-(4-methoxybenzyl)tetrazol-5-yl]phenyl]]-1,2,3,4,4a,10b-hexahydrobenzo[c][1,6]naphthyridine hydrochloride
EF: $C_{30}H_{32}N_6O_3 \times 1.25\ HCl \times 0.67\ H_2O$ MW: 582.30; m.p. 151–152° C.

Optical rotation:

$$[\alpha]_D^{20} = -5.75° (c = 1, \text{methanol}).$$

8. (−)-cis-8,9-Diethoxy-2-methyl-6-[4-(2H-2-cyclohexylmethyltetrazol-5-yl)phenyl]-1,2,3,4,4a,10b-hexahydrobenzo[c][1,6]naphthyridine hydrochloride
EF: $C_{31}H_{40}N_6O_2 \times 1.15\ HCl \times 1.20\ H_2O$, MW: 592.27; m.p. 172–180° C. (unsharp)

Optical rotation:

$$[\alpha]_D^{20} = -17.2° (c = 1, \text{methanol}).$$

9. (−)-(cis)-9-Ethoxy-8-methoxy-2-methyl-6-[4-(2H-2-ethyltetrazol-5-yl)phenyl]-1,2,3,4,4a,10b-hexahydrobenzo[c][1.6]naphthyridine
EF: $C_{25}H_{30}N_6O_2$, MW: 503.44: m.p. 151–152° C.
Optical rotation:

$$[\alpha]_D^{20} = -106.4° (c = 1, \text{methanol})$$

Melting point of the corresponding hydrochloride: EF: $C_{25}H_{30}N_6O_2 \times 1.03\ HCl \times 1.05\ H_2O$, MW: 503.44; m.p. 182–185° C. (unsharp)

10. (−)-cis-8-Ethoxy-9-methoxy-2-methyl-6-[4-(2H-2-ethyltetrazol-5-yl)-phenyl]-1,2,3,4,4a,10b-hexahydrobenzo[c][1.6]naphthyridine hydrochloride
EF: $C_{25}H_{30}N_6O_2 \times HCl \times 0.7\ H_2O$, MW: 495.68; m.p. 189–193° C. (unsharp)

Optical rotation:

$$[\alpha]_D^{20} = -75.9° (c = 1, \text{methanol})$$

11. (−)-cis-8,9-Diethoxy-2-methyl-6-[3-(2H-2-ethyltetrazol-5-yl)-phenyl]-1,2,3,4,4a,10b-hexahydrobenzo[c][1.6]naphthyridine hydrochloride
EF: $C_{25}H_{32}N_6O_2 \times 1.05\ HCl \times 0.6\ H_2O$, MW: 509.68; m.p. 140–153° C. (unsharp)

Optical rotation:

$$[\alpha]_D^{20} = -97.0° (c = 1, \text{methanol})$$

12. (−)-cis-9-Ethoxy-8-methoxy-2-methyl-6-[3-(2H-2-ethyltetrazol-5-yl)-phenyl]-1,2,3,4,4a,10b-hexahydrobenzo[c][1.6]naphthyridine hydrochloride
EF: $C_{25}H_{30}N_6O_2 \times HCl \times 0.75\ H_2O$, MW: 496.46; m.p. 146–160° C. (unsharp)

Optical rotation:

$$[\alpha]_D^{20} = -145.3° (c = 1, \text{methanol})$$

13. (−)-cis-8-Ethoxy-9-methoxy-2-methyl-6-[3-(2H-2-ethyltetrazol-5-yl)-phenyl]-1,2,3,4,4a,10b-hexahydrobenzo[c][1.6]napthyridine hydrochloride
EF: $C_{25}H_{30}N_6O_2 \times HCl \times 0.60\ H_2O$, MW: 493.83; m.p. 146° C. (unsharp)

Optical rotation:

$$[\alpha]_D^{20} = -117.1° (c = 1, \text{methanol})$$

14. (−)-cis-8,9-Dimethoxy-2-methyl-6-[3-(2H-2-ethyltetrazol-5-yl)-phenyl]-1,2,3,4,4a,10b-hexahydrobenzo[c][1.6]naphthyridine hydrochloride
EF: $C_{24}H_{28}N_6O_2 \times 1.03\ HCl \times 0.69\ H_2O$, MW: 482.47; m.p. 148–160° C.

Optical rotation:

$$[\alpha]_D^{20} = -92.2° (c = 1, \text{methanol})$$

15. (−)-cis-9-Ethoxy-8-methoxy-2-methyl-6-[4-(2H-2-hexyltetrazol-5-yl)-phenyl]-1,2,3,4,4a,10-hexahydrobenzo[c][1.6]naphthyridine hydrochloride
EF: $C_{29}H_{38}N_6O_2 \times 1.1\ HCl \times 0.5\ H_2O$, MW: 552.79: m.p. 120–135° C. (unsharp)

Optical rotation:

$$[\alpha]_D^{20} = -49.7° (c = 1, \text{methanol})$$

16. (−)-cis-9-Ethoxy-8-methoxy-2-6-[4-(2H-2-propyltetrazol-5-yl)-phenyl]-1,2,3,4,4a,10b-hexahydrobenzo[c][1.6]naphthyridine hydrochloride
EF: $C_{26}H_{32}N_6O_2 \times HCl \times 0.95\ H_2O$, MW: 552.79; m.p. 143–160° C. (unsharp)

Optical rotation:

$$[\alpha]_D^{20} = -60.0° (c = 1, \text{methanol})$$

The following two compounds are prepared analogously to the method described for compound 1.

17. (−)-cis-8,9-Diethoxy-2-methyl-6-[4-(1H- and 2H-2-tetrazol-5-yl)-phenyl]-1,2,3,4,4a,10b-hexahydrobenzo[c][1.6]naphthyridine
EF: $C_{24}H_{28}N_6O_2 \times 0.61\ H_2O$, MW: 443.5; m.p. 239–244° C. (unsharp)

Optical rotation:

$$[\alpha]_D^{20} = -62.3° (c = 1, \text{methanol})$$

18. (−)-cis-9-Ethoxy-8-methoxy-2-methyl-6-[4-(1H- and 2H-2-tetrazol-5-yl)-phenyl]-1,2,3,4,4a,10b-hexahydrobenzo[c][1.6]naphthyridine
EF: $C_{23}H_{26}N_6O_2 \times 1.43\ H_2O$, MW: 444.2; m.p. 225–232° C. (unsharp)

Optical rotation:

$$[\alpha]_D^{20} = -76.0°(c = 1, \text{methanol})$$

Starting Compounds
A. (−)-cis-6-(p-Cyanophenyl)-8,9-dimethoxy-2-methyl-1,2,3,4,4a,10b-hexahydrobenzo[c][1,6]-naphthyridine
Analogously to the process described in Example 2, the title compound is obtained when (−)-cis-3-(3,4-dimethoxyphenyl)-4-(4-cyanobenzamido)-1-methylpiperidine is employed for the condensation (compound C). M.p. 171–174° C.
EF: $C_{22}H_{23}N_3O_2$, MW: 361.45; m.p. 171–174° C.

B. (−)-cis-6-(p-Cyanophenyl)-8,9-diethoxy-2-methyl-1,2,3,4,4a,10b-hexahydrobenzo[c][1.6]-naphthyridine
Analogously to the process described in Example 2, the title compound is obtained when (−)-cis-3-(3,4-Diethoxyphenyl-4-(4-cyanobenzamido)-1-methylpiperidine (compound D) is employed for the condensation.
EF: $C_{24}H_{27}N_3O_2$, MW: 389.51;
Optical rotation:

$$[\alpha]_D^{20} = -55.2°(c = 1, \text{methanol})$$

C. (−)-cis-3-(3,4-Dimethoxyphenyl)-4-(4-cyanobenzamido)-1-methylpiperidine
A solution of 4-cyanobenzoyl chloride (prepared from 5.6 g of 4-cyanobenzoic acid and thionyl chloride) in 60 ml of dichloromethane is added dropwise at RT in the course of 10 min. to a solution of 10 g of (−)-cis-4-amino-3-(3,4-dimethoxyphenyl)-1-methylpiperidine prepared by extraction of the free base with dichloromethane after treating the corresponding dihydrochloride ($[\alpha]_D^{20}$=−57.1, c=1, methanol) with dilute sodium hydroxide solution) in 100 ml of dichloromethane and 5.6 ml of triethylamine. After stirring for about 2 h, the mixture is extracted with about 150 ml of saturated sodium hydrogencarbonate solution, and the organic phase is washed a further two times with 150 ml each time of water and dried over sodium sulfate. The viscous residue remaining after concentration is purified by column chromatography. The main product fraction concentrated in vacuo affords 11.2 g of residue forming a solid foam. The crystalline title compound is obtained by recrystallization in acetone.
EF: $C_{22}H_{25}N_3O_2$, MW: 379.46; m.p. 141° C.

D. (−)-cis-3-(3,4-Diethoxyphenyl-4-(4-cyanobenzamido)-1-methylpiperidine
Prepared analogously to compound C using (−)-cis-4-amino-3-(3,4-diethoxyphenyl)-1-methylpiperidine (compound U) as the amine component.
EF: $C_{24}H_{29}N_3O_3$, MW: 407.52; m.p. 119–121° C.

Starting from the corresponding 4-(alkyltetrazol-5-yl) benzoyl chlorides of the general formula R4—CO—X, the following title compounds are obtained analogously to Example C:

E. (−)-cis-3-(3,4-Dimethoxyphenyl)-4-[4-(2H-2-ethyltetrazol-5-yl)benzamido]-1-methylpiperidine
EF: $C_{24}H_{30}N_6O_3$, MW: 450.55; m.p. 166–167° C.
Optical rotation:

$$[\alpha]_D^{20} = -93.9°(c = 1, \text{methanol}).$$

F. (−)-cis-3-(3,4-Dimethoxyphenyl)-4-[4-(2H-2-methyltetrazol-5-yl)benzamido]-1-methylpiperidine
EF: $C_{23}H_{28}N_6O_3$, MW: 436.52; m.p. 155–157° C. (unsharp)

Optical rotation:

$$[\alpha]_D^{20} = -59.6°(c = 1, \text{methanol}).$$

G. (−)-cis-3-(3,4-Dimethoxyphenyl)-[4-[2H-2-(4-methoxybenzyl)tetrazol-5-yl]benzamido]-1-methylpiperidine
EF: $C_{30}H_{34}N_6O_4$, MW: 542.64; m.p. 153–154° C.
Optical rotation:

$$[\alpha]_D^{20} = -83.6°(c = 1, \text{methanol}).$$

H. (−)-cis-3-(3,4-Dimethoxy-phenyl)-4-[3-(2H-2-ethyltetrazol-5-yl)-benzamido]-1-methylpiperidine
EF: $C_{24}H_{30}N_6O_3$, MW: 450.54; m.p. 69–82° C. (unsharp)
Optical rotation:

$$[\alpha]_D^{20} = -28.2°(c = 1, \text{methanol}).$$

Starting from the corresponding 4-(alkyltetrazol-5-yl) benzoyl chlorides of the general formula R4—CO—X, the following title compounds are obtained analogously to the preparation process for compound C when (−)-cis-4-amino-3-(3,4-diethoxyphenyl)-1-methylpiperidine (compound U) having the optical rotation $$[\alpha]_D^{20} = -35.1°$$

(dihydrochloride, crude product in the form of a solid foam, c=1, methanol) is employed as the amine component.

I. (−)-cis-3(3,4-Diethoxyphenyl)-4-[4-(2H-2-ethyltetrazol-5-yl)benzamido]-1-methylpiperidine
EF: $C_{26}H_{34}N_6O_3$; MW: 478.60; m.p. 151.5–152.5° C.
Optical rotation:

$$[\alpha]_D^{20} = -91.4°(c = 1, \text{methanol}).$$

K. (−)-cis-3-(3,4-Diethoxyphenyl)-4-[4-(2H-2-methyltetrazol-5-yl)benzamido]-1-methylpiperidine
EF: $C_{25}H_{32}N_6O_3$, MW: 464.6; m.p. 176.5–177.5° C.
Optical rotation:

$$[\alpha]_D^{20} = -89.4°(c = 1, \text{methanol}).$$

L. (−)-cis-3-(3,4-Diethoxyphenyl)-[4-[2H-2-(4-methoxybenzyl)tetrazol-5-yl]benzamido]-1-methylpiperidine
EF: $C_{32}H_{38}N_6O_4$, MW: 570.7; m.p. 163.5–164.5° C.
Optical rotation:

$$[\alpha]_D^{20} = -80.8°(c = 1, \text{methanol}).$$

M. (−)-cis-3-(3,4-Diethoxyphenyl)-4-[4-(2H-2-cyclohexylmethyltetrazol-5-yl)benzamido]-1-methylpiperidine
EF: $C_{31}H_{42}N_6O_3$, MW: 546.72; m.p. 98–99° C.

Optical rotation:

$$[\alpha]_D^{20} = -83.5° (c = 1, \text{methanol}).$$

N. (−)-cis-3-(3,4-Diethoxyphenyl)-4-[4-(2H-2-ethyltetrazol-5-yl)-benzamido]-1-methylpiperidine
EF: $C_{26}H_{34}N_6O_3$, MW: 478.60; m.p. 136° C.
Starting from the corresponding 4-(alkyltetrazol-5-yl) benzoyl chlorides of the general formula R4—CO—X, the following title compounds are obtained analogously to the preparation process for compound C, when (−)-cis-4-amino-3-(3-ethoxy-4-methoxyphenyl)-1-methylpiperidine (compound V) is employed as the amine component.

O. (−)-cis-3-(3-Ethoxy-4-methoxyphenyl)-4-[4-(2H-2-ethyltetrazol-5-yl)-benzamido]-1-methylpiperidine
EF: $C_{25}H_{32}N_6O_3$, MW: 464.57; m.p. 165–167.5° C.
Optical rotation:

$$[\alpha]_D^{20} = -89.7° (c = 1, \text{methanol}).$$

P. (−)-cis-3-(3-Ethoxy-4-methoxyphenyl)-4-[3-(2H-2-ethyltetrazol-5-yl)-benzamido]-1-methylpiperidine
EF: $C_{25}H_{32}N_6O_3$, MW: 464.57; m.p. 137–138° C.
Optical rotation:

$$[\alpha]_D^{20} = -56.7° (c = 1, \text{methanol}).$$

Q. (−)-cis-3-(3-Ethoxy-4-methoxyphenyl)-4-[4-(2H-2-hexyltetrazol-5-yl)-benzamido]-1-methylpiperidine
EF: $C_{29}H_{40}N_6O_3$, MW: 520.68; m.p. 101.5–102.5° C.
Optical rotation:

$$[\alpha]_D^{20} = -85.3° (c = 1, \text{methanol}).$$

R. (−)-cis-3-(3-Ethoxy-4-methoxyphenyl)-4-[4-(2H-2-propyltetrazol-5-yl)-benzamido]-1-mehtylpiperidine
EF: $C_{26}H_{34}N_6O_3$, MW: 478.60; m.p. 160–161° C.
Optical rotation:

$$[\alpha]_D^{20} = -88.0° (c = 1, \text{methanol}).$$

Starting from the corresponding (4-alkyltetrazol-5-yl) benzoyl chlorides of the general formula R4—CO—X, the following title compounds are obtained analogously to the preparation process for compound C, when (−)-cis-4-amino-3-(3-methoxy-4-ethoxyphenyl)-1-methylpiperidine (compound W) is employed as the amine component.

S. (−)-cis-3-(3-Methoxy-4-ethoxyphenyl)-4-[4-(2H-2-ethyltetrazol-5-yl)-benzamidol-1-methylpiperidine
EF: $C_{25}H_{32}N_6O_3$, MW: 464.57; m.p. 183–184° C.

T. (−)-cis-3-(3-Methoxy-4-ethoxyphenyl)-4-[3-(2H-2-ethyltetrazol-5-yl)benzamido]-1-methylpiperidine
EF: $C_{25}H_{32}N_6O_3$, MW: 464.57; m.p. 135–136° C.
Optical rotation:

$$[\alpha]_D^{20} = -59.6° (c = 1, \text{methanol}).$$

The following three title compounds are obtained analogously to the process described in DE 42 17 401 when the corresponding 3,4-diethoxy-, 3-ethoxy-4-methoxy-, or the 3-methoxy-4-ethoxy-compounds are employed in the examples described there.

U. (−)-cis-4-Amino-3-(3,4-diethoxyphenyl)-1-methylpiperidine dihydrochloride
EF: $C_{16}H_{26}N_2O_2 \times 2HCl$; MW: 351.32; obtained as a crude product in the form of a solid foam; m.p.: from about 120° C. shrinkage and slow deliquescence, unsharp melting range up to about 150° C.; optical rotation:

$$[\alpha]_D^{20} = -35.1° (\text{dihydrochloride}, c = 1, \text{methanol}).$$

V. (−)-cis-4-Amino-3-(3-ethoxy-4-methoxyphenyl)-1-methylipieridine dihydrochloride
EF: $C_{15}H_{24}N_2O_2 \times 32\ HCl \times 0.96\ H_2O$, MW: 354.52; m.p. 252–254° C.
Optical rotation:

$$[\alpha]_D^{20} = -65.5° (c = 1, \text{methanol}).$$

W. (−)-cis-4-Amino-3-(3-methoxy-4-ethoxyphenyl)-1-methylpiperidine dihydrochloride
EF: $C_{15}H_{24}N_2O_2 \times 2\ HCl \times 0.32\ H_2O$, MW: 343.06; m.p. 241–243° C.
Optical rotation:

$$[\alpha]_D^{20} = -59.5° (c = 1, \text{methanol}).$$

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating and cilium-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumor necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin) neurogenic mediators (such as substance P, neurokinin), proteins such as, for example, granular contents of leukocytes (inter alia cationic proteins of eosinophils) and adherent proteins (e.g. integrins). The compounds according to the invention have smooth muscle-relaxant action. e.g. in the region of the bronchial system, of the blood circulation, and of the efferent urinary passages. Furthermore they have a cilium-frequency increasing action, e.g. in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma); disorders with a reduction of the cilium activity or with increased demands on the ciliar clearance (bronchitis, mucoviscidose); dermatoses (especially of proliferative, inflammatory and allergic type) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (Type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origin such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as antithrombotic, platelet aggregation-inhibiting substances.

The invention further relates to a method for the treatment of mammals including humans who are suffering from one of the abovementioned diseases. The method comprises administering a therapeutically effective and pharmacologically tolerable amount of one or more of the compounds according to the invention to the sick mammal.

The invention further relates to the compounds according to the invention for use in the treatment and/or prophylaxis of diseases, especially the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

Advantageously, the substances according to the invention are also suitable for combination with other substances which bring about stimulation of cAMP, such as prostaglandins (PGE2, PG12 and prostacyclin) and their derivatives, direct adenylate cyclase stimulators such as forskolin and related substances, or substances indirectly stimulating adenylate cyclase, such as catecholamines and adrenergic receptor agonists, in particular beta mimetics. In combination, on account of their cAMP degradation-inhibiting action, they in this case display a synergistic, superadditive activity. This comes to bear, for example, in their use in combination with PGE2 for the treatment of pulmonary hypertension.

The medicaments are prepared by methods known per se familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointments bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are used in particular in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gets or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.01 and 10 mg/kg per day.

Biological Investigations

In the investigation of PDE4 inhibition at the cellular level, the activation of inflammatory cells has particular importance. An example which may be mentioned is the FMLP (N-formylmethionylleucylphenylalanine)-induced superoxide production of neutrophilic granulocytes, which can be measured as luminol-potentiated chemiluminescence [McPhail L C, Strum S L, Leone P A and Sozzani S. The neutrophil respiratory burst mechanism. In "Immunology Series" 1992, 57, 47–76; ed. Coffey R G (Marcel Decker, Inc., New York-Basel-Hong Kong)].

Substances which inhibit chemiluminescence, and/or cytokine secretion, and/or the secretion of inflammationincreasing mediators in inflammatory cells, like T-lymphocytes, monocytes, macrophages and granulocytes are those which inhibit PDE4 or PDE3 and PDE4. The latter isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca. Naunyn-Schmiedebergs Arch Pharmacol 1991, 344, 682–690, Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-inhibitors. In "Phosphodiesterase Inhibitors", 147–160, "The Handbook of Immunopharmacology", Academic Press, 1996.

A. Methodology

1. Inhibition of PDE Isoenzymes

The PDE activity was determined according to Thompson et al. (1) with some modifications (2). The test samples contained 40 mM tris HCl (pH 7.4), 5 mM $MgCl_2$, 0.5 $\mu$M cAMP or cGMP, [$^3$H] cAMP or [$^3$H]cGMP (about 50,000 cpm/sample), the PDE isoenzyme-specific additions described in greater detail below, the indicated concentrations of inhibitor and an aliquot of the enzyme solution in a total sample volume of 200 $\mu$l. Stock solutions of the compounds to be investigated in DMSO were prepared in concentrations such that the DMSO content in the test samples did not exceed 1% by volume—to avoid an effect on the PDE activity. After preincubation at 37° C. for 5 minutes, the reaction was started by addition of the substrate (cAMP or cGMP). The samples were incubated at 37° C. for a further 15 min. The reaction was terminated by addition of 50 $\mu$l of 0.2N HCl. After cooling on ice for 10 minutes and addition of 25 $\mu$g of 5'-nucleotidase (snake venom from Crotalus atrox), the mixture was again incubated at 37° C. for 10 min and the samples were then applied to QAE Sephadex A-25 columns. The columns were eluted with 2 ml of 30 mM ammonium formate (pH 6.0). The radioactivity of the eluate was measured and corrected by the corresponding blank values. The proportion of hydrolyzed nucleotide in no case exceeded 20% of the original substrate concentration.

PDE1 ($Ca^{2+}$/calmodulin-dependent) from bovine brain: the inhibition of this isoenzyme was investigated in the presence of $Ca^{2+}$ (1 mM) and calmodulin (100 nM) using cGMP as a substrate (3).

PDE2 (cGMP-stimulated) from rat hearts was purified chromatographically Schudt et al. (4)] and investigated in the presence of cGMP (5 $\mu$M) using cAMP as a substrate.

PDE3 (cGMP-inhibited) and PDE5 (cGMP-specific) were investigated in homogenates of human blood platelets [Schudt et al. (4)] using cAMP or cGMP as a substrate.

PDE4 (cAMP-specific) was investigated in the cytosol of human polymorphonuclear leukocytes (PMNL) [isolated from leukocyte concentrates, see Schudt et al. (5)] using cAMP as a substrate. The PDE3 inhibitor motapizone (1 $\mu$M) was used in order to suppress the PDE3 activity emanating from contaminating blood platelets.

2. Statistics

The $IC_{50}$ values were determined from the concentration-inhibition curves by nonlinear regression using the GraphPad InPlot™ program (GraphPad Software Inc., Philadelphia, U.S.A.).

3. References (1) Thompson W. J., Terasaki W. L., Epstein P. M. and Strada S. J., Assay of cyclic nucleotide phosphodiesterase and resolution of multiple molecular forms of the enzyme; Adv. Cycl. Nucl. Res. 1979, 10, 69–92

(2) Bauer A. C. and Schwabe U., An improved assay of cyclic 3',5'-nucleotide phosphodiesterase with QAE Sephadex A-25; Naunyn-Schmiedeberg's Arch. Pharmacol. 1980, 311, 193–198

(3) Gietzen K., Sadorf I. and Bader H., A model for the regulation of the calmodulin-dependent enzymes erythrocyte $Ca^{2+}$-transport ATPase and brain phosphodiesterase by activators and inhibitors; Biochem. J. 1982, 207, 541–548.

(4) Schudt C., Winder S., Müller B. and Ukena D., Zardaverine as a selective inhibitor of phosphodiesterase isoenzymes; Biochem. Pharmacol. 1991, 42, 153–162

(5) Schudt C., Winder S., Forderkunz S., Hatzelmann A. and Ullrich V., Influence of selective phosphodiesterase inhibitors on human neutrophil functions and levels of cAMP and Ca; Naunyn-Schmiedeberg's Arch. Pharmacol. 1991, 344, 682–690

B. Results

In Table 1 which follows, the inhibitory concentrations determined according to Section A1 [inhibitory concentrations as -log $IC_{50}$ (mol/l)] for the compounds according to the invention are indicated for various PDE isoenzymes. The numbers of the compounds correspond to the numbers of the examples.

TABLE 1

| Compound | PDE4 [-log $IC_{50}$, mol/l] | PDE3 |
|---|---|---|
| 1 | 6.42 | 6.78 |
| 2 | 6.13 | 6.34 |
| 3 | 7.64 | 6.68 |
| 4 | 5.92 | 6.45 |
| 5 | 8.03 | 6.69 |
| 6 | 7.26 | 6.52 |
| 7 | 6.74 | 6.83 |
| 8 | 7.64 | 6.51 |
| 9 | 7.96 | 6.83 |
| 10 | 6.08 | 6.56 |
| 11 | 7.40 | 5.66 |
| 12 | 7.82 | 6.15 |
| 15 | 8.24 | 6.20 |
| 16 | 7.94 | 6.66 |
| 17 | 7.44 | 6.71 |
| 18 | 7.81 | 6.84 |

What is claimed is:

1. A compound of formula I

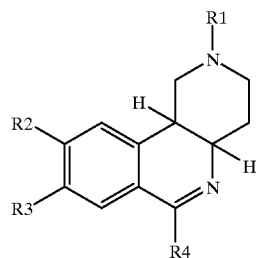

in which

R1 is 1–4C-alkyl,

R2 is hydroxyl, 1–4C-alkoxy, 3–7C-cycloalkoxy, 3–7C-cycloalkylmethoxy, or 1–4C-alkoxy which is completely or predominantly substituted by fluorine, R3 is hydroxyl, 1–4C-alkoxy, 3–7C-cycloalkoxy, 3–7C-cycloalkylmethoxy, or 1–4C-alkoxy which is completely or predominantly substituted by fluorine, or in which R2 and R3 together are a 1–2C-alkylenedioxy group, R4 is a phenyl radical substituted by R5, where R5 is a tetrazol-5-yl radical substituted by a radical R6, where R6 is hydrogen, 1–10C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, or a salt thereof.

2. A compound formula I as claimed in claim 1, in which

R1 is 1–4C-alkyl,

R2 is hydroxyl, 1–4C-alkoxy, 3–7C-cycloalkoxy. 3–7C-cycloalkylmethoxy, or 1–4C-alkoxy which is completely or predominantly substituted by fluorine, R3 is hydroxyl, 1–4C-alkoxy, 3–7C-cycloalkoxy, 3–7C-cycloalkylmethoxy or 1–4C-alkoxy which is completely or predominantly substituted by fluorine, or in which R2 and R3 together are a 1–2C-alkylenedioxy group, R4 is a phenyl radical substituted by R5, where R5 is a tetrazol-5-yl radical substituted by a radical R6, where R6 is hydrogen, 1–7C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, or a salt thereof.

3. A compound of formula I as claimed in claim 1, in which

R1 is 1–2C-alkyl,

R2 is 1–4C-alkoxy, 3–7C-cycloalkoxy, 3–7C-cycloalkylmethoxy, or 1–4C-alkoxy which is completely or predominantly substituted by fluorine, R3 is 1–4C-alkoxy, 3–7C-cycloalkoxy, 3–7C-cycloalkylmethoxy, or 1–4C-alkoxy which is completely or predominantly substituted by fluorine, or in which R2 and R3 together are a 1–2C-alkylenedioxy group, R4 is a phenyl radical substituted by R5, where R5 is a tetrazol-5-yl radical substituted by a radical R6, where R6 is hydrogen, 1–7C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, or a salt thereof.

4. A compound of formula I as claimed in claim 1, in which

R1 is methyl,

R2 is 1–4C-alkoxy, 3–7C-cycloalkoxy, 3–7C-cycloalkylmethoxy, or 1–2C-alkoxy which is completely or predominantly substituted by fluorine, R3 is 1–4C-alkoxy, 3–7C-cycloalkoxy, 3–7C-cycloalkylmethoxy, or 1–2C-alkoxy which is completely or predominantly substituted by fluorine, R4 is a phenyl radical substituted by R5, where R5 is a tetrazol-5-yl radical substituted by a radical R6, where R6 is hydrogen, 1–7C-alkyl, 5–7C-cycloalkyl, 3–7C-cycloalkylmethyl or Ar-1–2C-alkyl, where Ar is a phenyl radical which is unsubstituted or substituted by R7, and R7 is 1–2C-alkyl or 1–2C-alkoxy, or a salt thereof.

5. A compound of formula I as claimed in claim 1, in which

R1 is methyl,

R2 is 1–4C-alkoxy,

R3 is 1–4C-alkoxy,

R4 is a phenyl radical substituted by R5, where

R5 is a tetrazol-5-yl radical substituted by a radical R6, where

R6 is hydrogen, 1–7C-alkyl, cyclohexylmethyl or 4-methoxybenzyl, or a salt thereof.

6. A compound of formula I as claimed in claim 1, in which

R1 is methyl,

R2 is ethoxy,

R3 is methoxy or ethoxy,

R4 is a phenyl radical substituted by R5, where

R5 is a tetrazol-5-yl radical substituted by a radical R6, where

R6 is hydrogen, methyl, ethyl, propyl, hexyl, cyclohexylmethyl or 4-methoxybenzyl, or a salt thereof.

7. A compound of formula I as claimed in claim 1, in which the hydrogen atoms in the positions 4a and 10b are cis to one another, or a salt thereof.

8. A compound of formula I as claimed in claim 1, which in the positions 4a and 10b have the same absolute configuration as the compound (−)-cis-4-amino-3-(3,4-dimethoxyphenyl)-1-methylpiperidine dihydrochloride having the optical rotation $[\alpha]_D^{22} = -57.1°$ (c=1, methanol).

9. A medicament composition containing a compound as claimed in claim 1 together with a customary pharmaceutical auxilary and/or excipient.

10. A method of treating a subject afflicted with an airway disorder or a dermatosis amenable to treatment with a compound having PDE-inhibiting properties which comprises administering to the subject an effective amount of such compound, wherein the compound is a compound as claimed in claim 1 or a pharmaceutically-acceptable salt thereof.

11. In a method which comprises administering an effective amount of a benzonaphthyridine to a subject afflicted with an airway disorder or a dermatosis amenable to such treatment, the improvement wherein the benzonaphthyridine is a compound as claimed in claim 1 or a pharmaceutically-acceptable salt thereof.

12. A method of compounding a medicament composition for treating a subject afflicted with an airway disorder or a dermatosis which comprises combining a benzonaphthyridine with a customary pharmaceutical auxiliary and/or excipient, and wherein the benzonaphthyridine is a compound as claimed in claim 1 or a pharmacologically-acceptable salt thereof.

* * * * *